United States Patent
Zhang et al.

(10) Patent No.: US 7,570,998 B2
(45) Date of Patent: Aug. 4, 2009

(54) ACOUSTIC COMMUNICATION TRANSDUCER IN IMPLANTABLE MEDICAL DEVICE HEADER

(75) Inventors: Cheng Zhang, Vadnais Heights, MN (US); Thomas W. Piaget, Minneapolis, MN (US); Abhijeet V. Chavan, Maple Grove, MN (US); Keith R. Maile, New Brighton, MN (US); Ron A. Balczewski, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/780,903

(22) Filed: Jul. 20, 2007

(65) Prior Publication Data
US 2008/0021289 A1 Jan. 24, 2008

Related U.S. Application Data

(63) Continuation-in-part of application No. 11/212,176, filed on Aug. 26, 2005.

(60) Provisional application No. 60/820,062, filed on Jul. 21, 2006.

(51) Int. Cl.
*A61N 1/00* (2006.01)
(52) U.S. Cl. ........................................ 607/18
(58) Field of Classification Search ............... 607/60, 607/32, 36, 37, 18
See application file for complete search history.

(56) References Cited

U.S. PATENT DOCUMENTS

| | | | |
|---|---|---|---|
| 2,967,957 A | 1/1961 | Massa | |
| 3,568,661 A | 3/1971 | Franklin | |
| 3,676,720 A | 7/1972 | Libby et al. | |
| 3,757,770 A | 9/1973 | Brayshaw et al. | |
| 3,792,204 A | 2/1974 | Murayama et al. | |
| 3,798,473 A | 3/1974 | Murayama et al. | |
| 3,832,580 A | 8/1974 | Yamamuro et al. | |
| 3,894,198 A | 7/1975 | Murayama et al. | |
| 3,940,637 A | 2/1976 | Ohigashi et al. | |
| 3,978,353 A | 8/1976 | Kinoshita | |
| 4,008,408 A | 2/1977 | Kodama | |

(Continued)

FOREIGN PATENT DOCUMENTS

DE     3222349     1/1984

(Continued)

OTHER PUBLICATIONS

International Search Report and Written Opinion of International No. PCT/US2006/033273, filed Aug. 25, 2006, both mailed Jan. 19, 2007.

(Continued)

*Primary Examiner*—Mark W Bockelman
*Assistant Examiner*—Roland Dinga
(74) *Attorney, Agent, or Firm*—Faegre & Benson LLP

(57) ABSTRACT

An implantable medical device is adapted for implantation into body tissue. The implantable medical device comprises a housing and a header coupled to the housing. A cavity is located in the header. An ultrasonic transducer adapted to transmit acoustic waves at a communication frequency is located in the cavity, and a coupling surface is interposed between the ultrasonic transducer and the body tissue and is acoustically coupled with the body tissue.

19 Claims, 6 Drawing Sheets

U.S. PATENT DOCUMENTS

| | | |
|---|---|---|
| 4,051,455 A | 9/1977 | Fowler |
| 4,056,742 A | 11/1977 | Tibbetts |
| 4,064,375 A | 12/1977 | Russell et al. |
| 4,096,756 A | 6/1978 | Alphonse |
| 4,127,110 A | 11/1978 | Bullara |
| 4,170,742 A | 10/1979 | Itagaki et al. |
| 4,181,864 A | 1/1980 | Etzold |
| 4,227,407 A | 10/1980 | Drost |
| 4,281,484 A | 8/1981 | Massa |
| 4,431,873 A | 2/1984 | Dunn et al. |
| 4,433,400 A | 2/1984 | De Reggi et al. |
| 4,456,850 A | 6/1984 | Inoue et al. |
| 4,481,950 A | 11/1984 | Duggan |
| 4,517,665 A | 5/1985 | De Reggi et al. |
| 4,519,401 A | 5/1985 | Ko et al. |
| 4,541,431 A | 9/1985 | Ibrahim et al. |
| 4,558,249 A | 12/1985 | Lerch et al. |
| 4,580,074 A | 4/1986 | Gilman |
| 4,593,703 A | 6/1986 | Cosman |
| 4,600,855 A | 7/1986 | Strachan |
| 4,642,508 A | 2/1987 | Suzuki et al. |
| 4,653,036 A | 3/1987 | Harris et al. |
| 4,653,508 A | 3/1987 | Cosman |
| 4,660,568 A | 4/1987 | Cosman |
| 4,672,976 A | 6/1987 | Kroll |
| 4,676,255 A | 6/1987 | Cosman |
| 4,677,337 A | 6/1987 | Kleinschmidt et al. |
| 4,781,715 A | 11/1988 | Wurzel |
| 4,793,825 A | 12/1988 | Benjamin et al. |
| 4,835,435 A | 5/1989 | Yeung et al. |
| 4,846,191 A | 7/1989 | Brockway et al. |
| 4,911,172 A | 3/1990 | Bui et al. |
| 4,958,100 A | 9/1990 | Crawley et al. |
| 5,012,815 A | 5/1991 | Bennett, Jr. et al. |
| 5,024,224 A | 6/1991 | Engebretson |
| 5,088,576 A | 2/1992 | Potthoff et al. |
| 5,113,859 A | 5/1992 | Funke |
| 5,160,870 A | 11/1992 | Carson et al. |
| 5,178,153 A | 1/1993 | Einzig |
| 5,283,397 A | 2/1994 | Pavlovic |
| 5,289,821 A | 3/1994 | Swartz |
| 5,300,875 A | 4/1994 | Tuttle |
| 5,314,457 A | 5/1994 | Jeutter et al. |
| 5,339,290 A | 8/1994 | Greenstein |
| 5,367,500 A | 11/1994 | Ng |
| 5,381,067 A | 1/1995 | Greenstein et al. |
| 5,381,386 A | 1/1995 | Lum et al. |
| 5,410,587 A | 4/1995 | Grunwell |
| 5,411,551 A | 5/1995 | Winston et al. |
| 5,423,334 A | 6/1995 | Jordan |
| 5,438,553 A | 8/1995 | Wilson et al. |
| 5,476,488 A | 12/1995 | Morgan et al. |
| 5,483,501 A | 1/1996 | Park et al. |
| 5,488,954 A | 2/1996 | Sleva et al. |
| 5,495,137 A | 2/1996 | Park et al. |
| 5,554,177 A | 9/1996 | Kieval et al. |
| 5,562,714 A | 10/1996 | Grevious |
| 5,571,152 A | 11/1996 | Chen et al. |
| 5,628,782 A | 5/1997 | Myers |
| 5,679,026 A * | 10/1997 | Fain et al. .................. 439/651 |
| 5,704,352 A | 1/1998 | Tremblay et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,749,909 A | 5/1998 | Schroeppel et al. |
| 5,757,104 A | 5/1998 | Getman et al. |
| 5,792,195 A | 8/1998 | Carlson et al. |
| 5,807,258 A | 9/1998 | Cimochowski et al. |
| 5,825,117 A | 10/1998 | Ossmann et al. |
| 5,832,924 A | 11/1998 | Archibald et al. |
| 5,833,603 A | 11/1998 | Kovacs et al. |
| 5,843,135 A | 12/1998 | Weijand et al. |
| 5,873,835 A | 2/1999 | Hastings et al. |
| 5,879,283 A | 3/1999 | Adams et al. |
| 5,935,081 A | 8/1999 | Kadhiresan |
| 5,956,292 A | 9/1999 | Bernstein |
| 5,957,950 A | 9/1999 | Mockros et al. |
| 5,967,986 A | 10/1999 | Cimochowski et al. |
| 6,044,298 A | 3/2000 | Salo et al. |
| 6,053,873 A | 4/2000 | Govari et al. |
| 6,058,329 A | 5/2000 | Salo et al. |
| 6,068,589 A | 5/2000 | Neukermans |
| 6,082,367 A | 7/2000 | Greeninger et al. |
| 6,140,740 A | 10/2000 | Porat et al. |
| 6,185,452 B1 | 2/2001 | Schulman et al. |
| 6,223,081 B1 * | 4/2001 | Kerver ........................ 607/17 |
| 6,409,675 B1 | 6/2002 | Turcott |
| 6,475,170 B1 | 11/2002 | Doron et al. |
| 6,477,406 B1 * | 11/2002 | Turcott ....................... 600/518 |
| 6,480,733 B1 | 11/2002 | Turcott |
| 6,486,588 B2 | 11/2002 | Doron et al. |
| 6,527,729 B1 | 3/2003 | Turcott |
| 6,537,200 B2 | 3/2003 | Leysieffer et al. |
| 6,554,761 B1 | 4/2003 | Puria et al. |
| 6,575,894 B2 | 6/2003 | Leysieffer et al. |
| 6,600,949 B1 | 7/2003 | Turcott |
| 6,628,989 B1 | 9/2003 | Penner et al. |
| 6,629,922 B1 | 10/2003 | Puria et al. |
| 6,643,548 B1 | 11/2003 | Mai et al. |
| 6,645,145 B1 * | 11/2003 | Dreschel et al. ............. 600/443 |
| 6,654,638 B1 * | 11/2003 | Sweeney ....................... 607/9 |
| 6,671,550 B2 | 12/2003 | Iaizzo et al. |
| 6,697,674 B2 | 2/2004 | Leysieffer |
| 6,740,076 B2 * | 5/2004 | Hoben et al. .............. 604/891.1 |
| 6,741,714 B2 | 5/2004 | Jensen |
| 6,763,722 B2 | 7/2004 | Fjield et al. |
| 6,764,446 B2 * | 7/2004 | Wolinsky et al. ............ 600/300 |
| 7,016,739 B2 | 3/2006 | Bange et al. |
| 7,024,248 B2 | 4/2006 | Penner et al. |
| 7,035,684 B2 | 4/2006 | Lee |
| 7,107,103 B2 | 9/2006 | Schulman et al. |
| 7,114,502 B2 | 10/2006 | Schulman et al. |
| 7,118,531 B2 | 10/2006 | Krill |
| 7,198,603 B2 | 4/2007 | Penner et al. |
| 7,220,232 B2 | 5/2007 | Suorsa et al. |
| 7,228,175 B2 | 6/2007 | Jain et al. |
| 7,236,821 B2 | 6/2007 | Cates |
| 7,283,874 B2 | 10/2007 | Penner |
| 7,335,169 B2 | 2/2008 | Thompson et al. |
| 2002/0027400 A1 * | 3/2002 | Toda .......................... 310/334 |
| 2002/0036446 A1 * | 3/2002 | Toda et al. .................. 310/328 |
| 2002/0151938 A1 | 10/2002 | Corbucci |
| 2002/0177782 A1 | 11/2002 | Penner |
| 2003/0055461 A1 | 3/2003 | Girouard et al. |
| 2004/0103906 A1 | 6/2004 | Schulman et al. |
| 2004/0106954 A1 | 6/2004 | Whitehurst et al. |
| 2004/0106960 A1 | 6/2004 | Siejko et al. |
| 2004/0106961 A1 | 6/2004 | Siejko et al. |
| 2004/0122315 A1 * | 6/2004 | Krill ........................... 600/437 |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167416 A1 | 8/2004 | Lee |
| 2004/0172083 A1 * | 9/2004 | Penner ......................... 607/35 |
| 2004/0204744 A1 * | 10/2004 | Penner et al. ................. 607/23 |
| 2004/0230249 A1 | 11/2004 | Haefner |
| 2005/0102001 A1 | 5/2005 | Maile et al. |
| 2005/0131472 A1 | 6/2005 | Ding et al. |
| 2005/0137490 A1 | 6/2005 | Scheiner et al. |
| 2005/0148896 A1 | 7/2005 | Siejko et al. |
| 2005/0149136 A1 | 7/2005 | Siejko et al. |
| 2005/0149138 A1 | 7/2005 | Min et al. |
| 2006/0009818 A1 * | 1/2006 | Von Arx et al. ............... 607/60 |
| 2006/0082259 A1 | 4/2006 | Schlenke |

| | | | |
|---|---|---|---|
| 2006/0142819 | A1 | 6/2006 | Penner et al. |
| 2006/0149329 | A1* | 7/2006 | Penner .................. 607/32 |
| 2007/0049977 | A1 | 3/2007 | Von Arx et al. |
| 2008/0021509 | A1 | 1/2008 | Mi et al. |
| 2008/0021510 | A1 | 1/2008 | Mi et al. |

FOREIGN PATENT DOCUMENTS

| | | |
|---|---|---|
| EP | 0798016 | 10/1997 |
| EP | 0897690 | 2/1999 |
| EP | 1151719 | 11/2001 |
| WO | WO 83/03345 | 10/1983 |
| WO | WO 97/01986 | 1/1997 |
| WO | WO 97/33513 | 9/1997 |
| WO | 97/35636 | 10/1997 |
| WO | WO 97/47236 | 12/1997 |
| WO | WO 98/26716 | 6/1998 |
| WO | WO 98/29030 | 7/1998 |
| WO | WO 99/26530 | 6/1999 |
| WO | WO 99/59460 | 11/1999 |
| WO | WO 00/16686 | 3/2000 |
| WO | WO 03/068047 | 8/2003 |
| WO | 2004/091719 | 10/2004 |
| WO | WO 2006/069215 | 6/2006 |

OTHER PUBLICATIONS

Robert D. Blevins Ph.D., "Formulas for Natural Frequency and Mode Shape", ISBN: 1-57524-184-6.

Search Report and Written Opinion of PCT/US2007/073989, filed Jul. 20, 2007, both mailed Dec. 20, 2007.

Search Report and Written Opinion of PCT/US2007/073998, filed Jul. 20, 2007, both mailed Mar. 6, 2008.

C. Hierold et al (Germany, 1998) "Implantable Low Power Integrated Pressure Sensor System for Minimal Invasive Telemetric Patient Monitoring" IEEE, pp. 568-573.

Cassereau et al., "Time Reversal of Ultrasonic Fields—Part 3: Theory of the Closed Time-Reversal Cavity," IEEE Transactions on Ultrasonics, Ferroelectrics, and Frequency Control, vol. 39, No. 5, Sep. 1992, pp. 579-592.

ER. Cosman et al (Massachussetts, Apr. 1979) "A Telemetric Pressure Sensor for Ventricular Shunt Systems" Surgical Neurology, vol. 11, No. 4, pp. 287-294.

Fink et al., "Time Reversal Acoustics," 2004 IEEE Transactions on Ultrasonics, Ferroelectrics, and Frequency Control Joint 50th Anniversary Conference, Ultrasonics Symposium, pp. 850-859.

Fink, "Time Reversal of Ultrasonic Fields—Part 1: Basic Principles," IEEE Transactions on Ultrasonics, Ferroelectrics, and Frequency Control, vol. 39, No. 5, Sep. 1992, pp. 555-566.

G. W. H. Schurink et al (1998) "Late Endoleak after Endovascular Therapy for Abdominal Aortic Aneurysm" Eur. J. Vasc. Endovasc. Surg. vol. 17, pp. 448-450.

GH White et al (1997) "Endoleak Following Endoluminal Repair of AAA: Management Options and Patient Outcomes", J. Endovasc Surg. p. 1-45.

Karl E. Richard et al (Germany, Jan. 1999) "First clinical results with a telemetric shunt-integrated ICP-sensor" Neurological Research vol. 21, pp. 117-120.

Prof. Dr. Johannes Zacheja et al (Germany, Sep. 1996) "An Implantable Microsystem for Biomedical Applications" Micro System Technologies 96, pp. 717-722.

S. K. Gupta et al (1999) "Use of a Piezoelectric Film Sensor for Monitoring Vascular Grafts" The American Journal of Surgery vol. 160, pp. 182-186.

T. Chuter et al (Sweden, Jan. 1997) "Aneurysm Pressure following Endovascular Exclusion" Eur. J. Vasc. Endovasc. Surg. vol. 13, pp. 85-87.

T.A. Cochran et al (1990) "Aortic Aneurysm Abdominal", Current Therapy in Adult Medicine, Fourth Edition.

Wu et al., "Time Reversal of Ultrasonic Fields—Part 2: Experimental Results," IEEE Transactions on Ultrasonics, Ferroelectrics, and Frequency Control, vol. 39, No. 5, Sep. 1992, pp. 567-578.

Z. Tang et al (May 1995) "Data Transmission from an Implantable Biotelemeter by Load-Shift Keying Using Circuit Configuration Modulator" IEEE Transactions on Biomedical Engineering, vol. 42, No. 5, pp. 524-528.

* cited by examiner

ACOUSTIC COMMUNICATION TRANSDUCER IN IMPLANTABLE MEDICAL DEVICE HEADER

CROSS-REFERENCE TO RELATED APPLICATION

This application claims priority to Provisional Application No. 60/820,062, filed Jul. 21, 2006, and is a continuation-in-part application of application Ser. No. 11/212,176, filed Aug. 26, 2005, both of which are herein incorporated by reference in their entirety.

PARTIES TO A JOINT RESEARCH AGREEMENT

The claimed invention was made subject to a joint research agreement between Cardiac Pacemakers, Inc. and Remon Medical Technologies Ltd.

TECHNICAL FIELD

The present invention relates to transducers used in combination with an implantable medical device to wirelessly communicate between the implantable medical device and remote sensors implanted in the body or other implantable medical devices. The present invention more particularly relates to transducers located in the header of the implantable medical device.

BACKGROUND

Implantable medical devices are often used to treat a variety of medical conditions. Examples of implantable medical devices include drug delivery devices, pain management devices, and devices that treat heart arrhythmias. One example of an implantable medical device used to treat heart arrhythmias is a cardiac pacemaker, which is commonly implanted in a patient to treat bradycardia (i.e., abnormally slow heart rate). A pacemaker includes a pulse generator and leads, which form the electrical connection between the pulse generator and the heart. An implantable cardioverter defibrillator ("ICD") is used to treat tachycardia (i.e., abnormally rapid heart rate). An ICD also includes a pulse generator and leads that deliver electrical energy to the heart. Pulse generators typically include a housing for a battery and electrical circuitry and a header for connecting the leads to the pulse generator.

Implantable medical devices are also useful in the treatment of heart failure. For example, cardiac resynchronization therapy ("CRT") (also commonly referred to as biventricular pacing) is an emerging treatment for heart failure, which involves stimulation of both the right and the left ventricles to increase hemodynamic efficiency and cardiac output. The treatment of heart failure and heart arrhythmias can be enhanced through the use of chronically implanted sensors. For example, it can be useful to place a pressure sensor in the vasculature because the diastolic pressure can be a good predictor of decompensation in heart failure patients. Pressure sensors can also be used as part of pacing or defibrillation therapy. Communication between the implantable medical device and the chronically implanted sensor can allow the sensor data to be downloaded by a clinician or used to modify the therapy delivered by the implantable medical device. There is therefore a need for an implantable medical device that includes a transducer for communication with a chronically implanted sensor.

SUMMARY

The present invention, according to one embodiment, is an implantable medical device adapted for implantation into body tissue. The implantable medical device comprises a housing and a header coupled to the housing. A cavity is located in the header. An ultrasonic transducer adapted to transmit acoustic waves at a communication frequency is located in the cavity, and a coupling surface is interposed between the ultrasonic transducer and the body tissue and is acoustically coupled with the body tissue.

According to another embodiment, the present invention is an implantable medical device for implantation into body tissue. The implantable medical device comprises a housing and a header coupled to the housing. A cavity is located in the header and a means for transmitting an ultrasonic signal is located in the cavity. A coupling surface is interposed between the means for transmitting an ultrasonic signal and the body tissue and is acoustically coupled with the body tissue.

The present invention, according to yet another embodiment, is an implantable medical device for implantation into body tissue. The implantable medical device comprises a housing, a header coupled to the housing, and a tab coupled to the housing. A cavity is located in the tab and an ultrasonic transducer adapted to transmit acoustic waves at a communication frequency is located in the cavity. A coupling surface is interposed between the ultrasonic transducer and the body tissue and is acoustically coupled with the body tissue.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
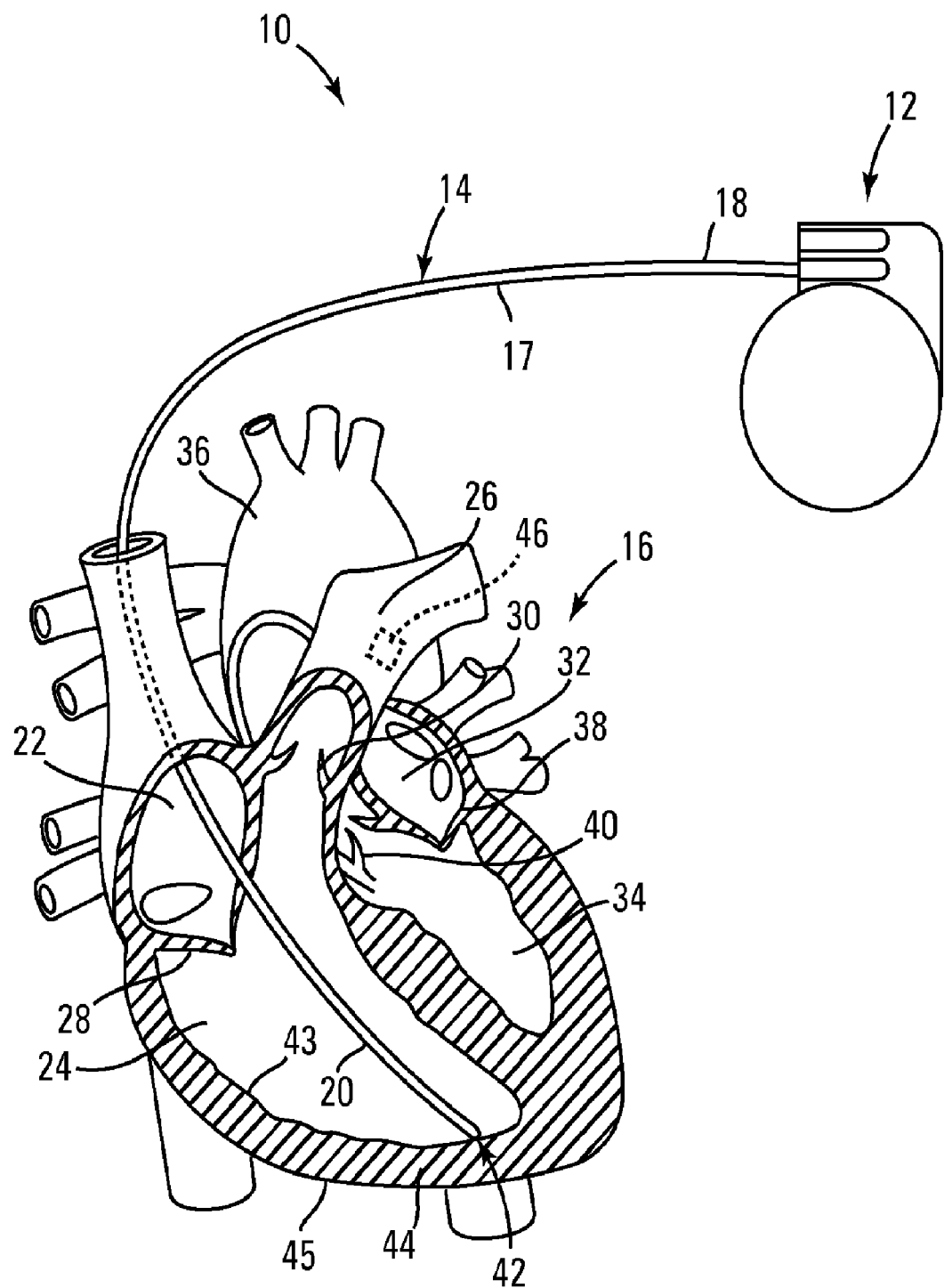
FIG. 1 is a combined cutaway and perspective view of an implantable medical device in accordance with one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical device (IMD) 10. The IMD 10 includes a pulse generator 12 and a cardiac lead 14. The lead 14 operates to convey electrical signals between the heart 16 and the pulse generator 12. A proximal end 18 of the lead 14 is coupled to the pulse generator 12 and a distal end 20 is coupled to the heart 16. The lead 14 includes a lead body 17 extending from the lead proximal end 18 to the lead distal end 20.

The heart 16 includes a right atrium 22, a right ventricle 24, and a pulmonary artery 26. A tricuspid valve 28 is located between and controls the flow of blood from the right atrium 22 and the right ventricle 24. A pulmonic valve 30 is located between and controls the flow of blood from the right ventricle 24 to the pulmonary artery 26. The heart 16 also includes a left atrium 32, a left ventricle 34, and an aorta 36. A mitral valve 38 is located between and controls the flow of blood from the left atrium 32 to the left ventricle 34. An aortic valve 40 is located between and controls the flow of blood from the left ventricle 34 to the aorta 36. In the embodiment shown, the IMD 10 includes one lead 14, but in other embodiments, the IMD 10 includes a plurality of leads 14. For example, it may include a first lead 14 adapted to convey electrical signals between the pulse generator 12 and the left ventricle 34 and a second lead 14 adapted to convey electrical signals between the pulse generator 12 and the right ventricle 24.

In the embodiment shown in FIG. 1, a helical electrode 42 penetrates the endocardium 43 of the right ventricle 24 and is embedded in the myocardium 44 of the heart 16. When positioned as above, the electrode 42 can be used to sense the electrical activity of the heart 16 or to apply a stimulating pulse to the right ventricle 24. In other embodiments, the cardiac lead 14 of the present invention can also be implanted in any other portion of the heart 16 as known in the art. For example, it may be implanted in the right atrium 22, the right ventricle 24, the pulmonary artery 26, the left ventricle 34, or in the coronary veins. In one embodiment, the IMD 10 includes multiple electrodes 42 disposed to sense electrical activity and/or deliver therapy to the left and right sides of the heart 16 or to both sides of the heart 16. In one embodiment, the lead 14 can be an epicardial lead where the electrode 42 penetrates the epicardium 45. While the IMD 10 shown in FIG. 1 is a cardiac pacemaker, in other embodiments, the IMD 10 could comprise any other medical device suitable for implantation in the body.

As shown in FIG. 1, a remote device 46 is located in the pulmonary artery 26. Alternatively, the device 46 could be located in the right ventricle 24, the aorta 36, or any other location in or near the heart 16 or vasculature. The device 46 could sense pressure or could alternatively comprise a volume sensor or sense any other cardiac parameter, such as maximum or minimum pressure, or calculate a cardiac parameter derivative, such as the slope of the pressure. In other embodiments, the device 46 can be located anywhere in the body adapted for sensing a desired biological parameter. For example the device 46 could be used to sense or monitor other biological functions, such as glucose level. The device 46 shown in FIG. 1 can be a remote pressure sensor used to sense pressure in the pulmonary artery 26. The sensed pressure can be used to predict decompensation of a heart failure patient or to optimize pacing or defibrillation therapy. One example of a remote pressure sensor 46 adapted to measure pressure is disclosed in U.S. Pat. No. 6,764,446 to Wolinsky et al.

Figure 2:
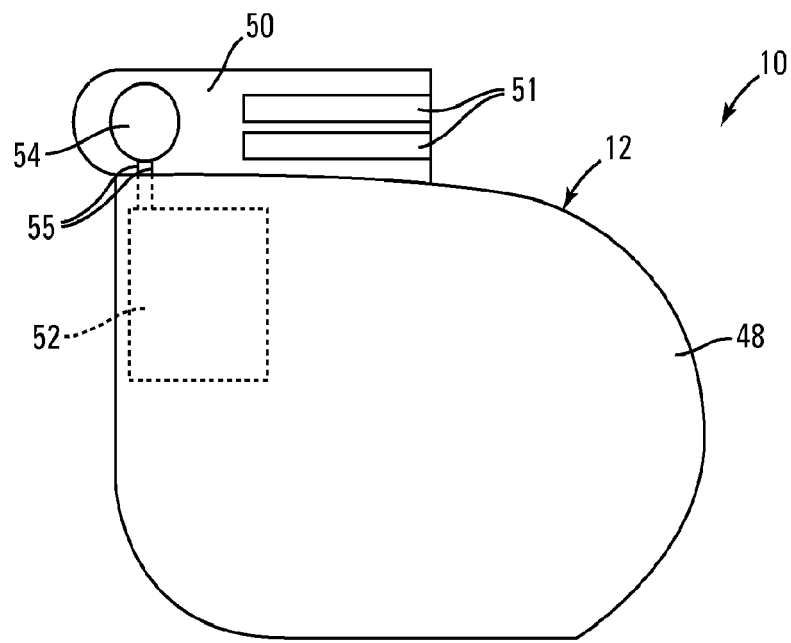
FIG. 2 shows a front view of an implantable medical device having an acoustic transducer located in the header according to one embodiment of the present invention.

FIG. 2 depicts a front view of one embodiment of the pulse generator 12 of FIG. 1. As shown in FIG. 2, the pulse generator 12 includes a housing 48 and a header 50. The housing 48 includes control circuitry 52. The header 50 includes connectors 51 for connection to the lead 14 or leads 14. An acoustic transducer 54 is located in the header 50, which is connected to the control circuitry 52 via the electrical feedthroughs 55. In one embodiment, the acoustic transducer 54 sends and receives acoustic signals at a frequency above about 20 kiloHertz. In another embodiment, the acoustic transducer 54 sends and receives acoustic signals at a frequency of about 40 kiloHertz. The acoustic transducer 54 shown in FIG. 2 has a circular shape, but alternatively could have any other shape, including square, rectangular, triangular, or irregular. The acoustic transducer 54 can comprise any piezoelectric material. In one embodiment, the acoustic transducer 54 can comprise a polyvinylidine diflouride (PVDF) material. One acoustic transducer comprised of PVDF material is disclosed in U.S. Patent Application Publication No. 2002/0036446 to Toda et al., herein incorporated by reference in its entirety. In another embodiment, the acoustic transducer 54 can comprise a lead zirconate titanate (PZT) material. One acoustic transducer comprised of PZT material is disclosed in U.S. Patent Application Publication No. 2002/0027400 to Toda, herein incorporated by reference in its entirety. Alternatively, the acoustic transducer 54 can comprise a capacitor micromachined ultrasonic transducer (cMUT) or any other transducer as is known in the art.

Figure 3:
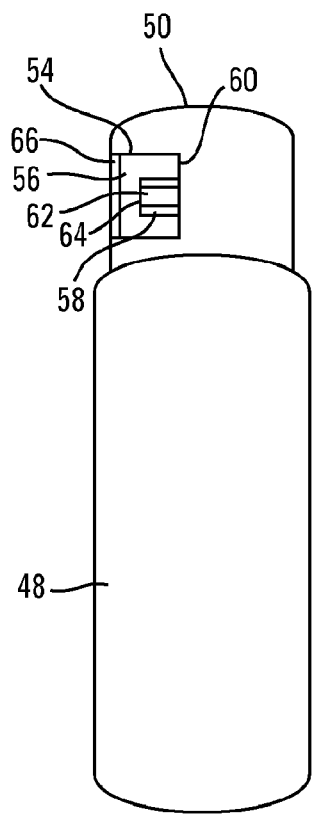
FIG. 3 shows a cross-sectional view of one embodiment of the implantable medical device of FIG. 2.

A cross-sectional view of one embodiment of the implantable medical device 10 is shown in FIG. 3. In the embodiment shown in FIG. 3, the acoustic transducer 54 comprises a PVDF transducer. A cavity 56 is located in the header 50. A ceramic or silicon substrate 58 is located against a back wall 60 of the cavity 56. The substrate 58 includes an aperture 62, and a PVDF material 64 is disposed over and covers the aperture 62. The PVDF material 64 can be coupled to the substrate 58 using epoxy or medical adhesive. In one embodiment, the PVDF material 64 can comprise a bimorph structure having two layers of PVDF material. The cavity 56 can be filled with water, oil, an acoustic gel, or any other medium or material adapted for transmitting acoustic waves. In one embodiment, the cavity 56 can be filled with any biocompatible material adapted for transmitting acoustic waves.

A coupling surface 66 is disposed over and covers the cavity 56. In one embodiment, the coupling surface 66 comprises any surface capable of propagating acoustic pressure between the medium of cavity 56 and body tissue. In one embodiment, the coupling surface 66 can comprise a thin titanium diaphragm. In other embodiments, the coupling surface 66 comprises any biocompatible material having dimensions capable of propagating acoustic pressure between the medium of cavity 56 and body tissue. One example of PVDF material adapted for use in the acoustic transducer can be obtained from Measurement Specialties, Inc., located at 950 Forge Avenue, Norristown, Pa. 19403.

Figure 4:
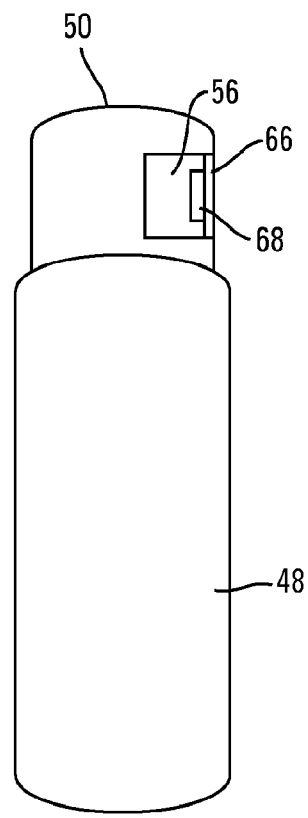
FIG. 4 shows a cross-sectional view of another embodiment of the implantable medical device of FIG. 2.

FIG. 4 depicts an alternative embodiment of the implantable medical device of FIG. 2. In this embodiment, the acoustic transducer 54 comprises a PZT material 68. A cavity 56 is located in the header 50 and is covered by a coupling surface 66. The PZT material 68 is coupled to the coupling surface 66. The PZT material 68 can be coupled to the coupling surface 66 using epoxy or any medical adhesive. The cavity 56 can be filled with air, nitrogen, or any other gas. Alternatively, the cavity 56 can comprise a vacuum. In the embodiment shown in FIG. 4, the coupling surface 66 comprises a resonant surface that resonates at the acoustic communication frequency. In one embodiment, this frequency is above 20 kiloHertz. In another embodiment, this frequency is about 40 kiloHertz.

Figure 5:
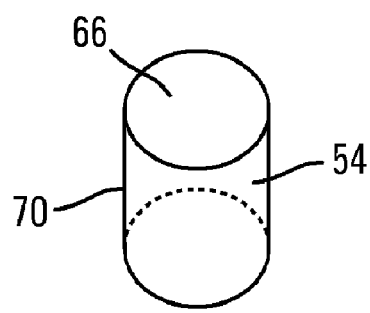
FIG. 5 shows a perspective view of one embodiment of the ultrasonic transducer of FIG. 2.

An alternative structure for the acoustic transducer 54 is shown in FIG. 5. In this embodiment, the acoustic transducer 54 is located inside a casing 70. The casing 70 can be inserted into the cavity 56 located in the header 50. The casing 70 can comprise titanium or any other suitable material. The coupling surface 66 is disposed over the casing 70. The acoustic transducer 54 structure inside the casing 70 can comprise the structures discussed with respect to FIGS. 3 and 4, or could comprise any other acoustic transducer structure as is known in the art. The casing 70 has a cylindrical shape in FIG. 5, but can have any shape adapted to fit the shape of the acoustic transducer 54.

Figure 6:
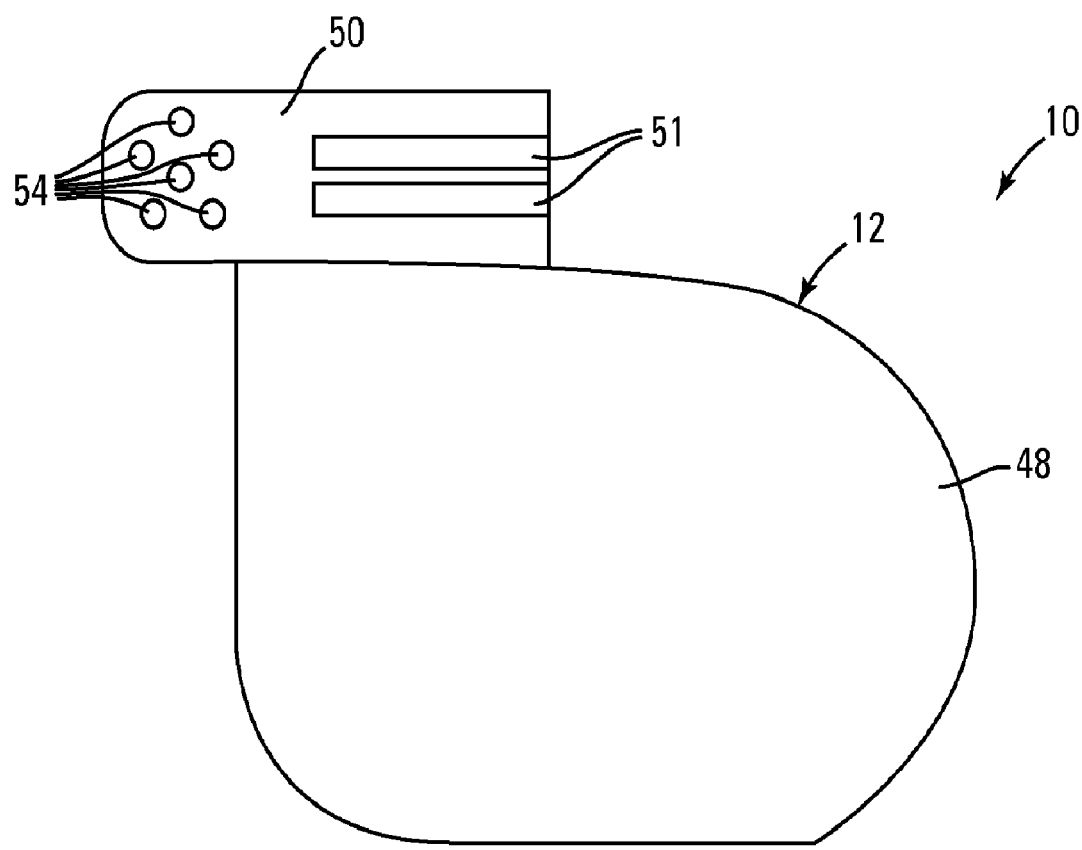
FIG. 6 shows a front view of yet another embodiment of an implantable medical device according to the present invention.

FIG. 6 depicts another embodiment of the implantable medical device 10 of the present invention. In this embodiment, a plurality of acoustic transducers 54 are located in the header 50. The acoustic transducers 54 may comprise the acoustic transducers discussed with respect to FIG. 3, FIG. 4, or any combination of FIGS. 3 and 4. The plurality of acoustic transducers 54 could also include cMUT transducers or other types of acoustic transducers as is known in the art. Acoustic transducers 54 could be located on multiple surfaces of the header 50. Six circular acoustic transducers 54 are shown in FIG. 4, but any number of any shape of transducers could be used. If desired, the acoustic transducers 54 can include casings 70. Such an arrangement allows the acoustic transducer 54 to act in parallel, which results in better resonance and amplification characteristics.

Figure 7:
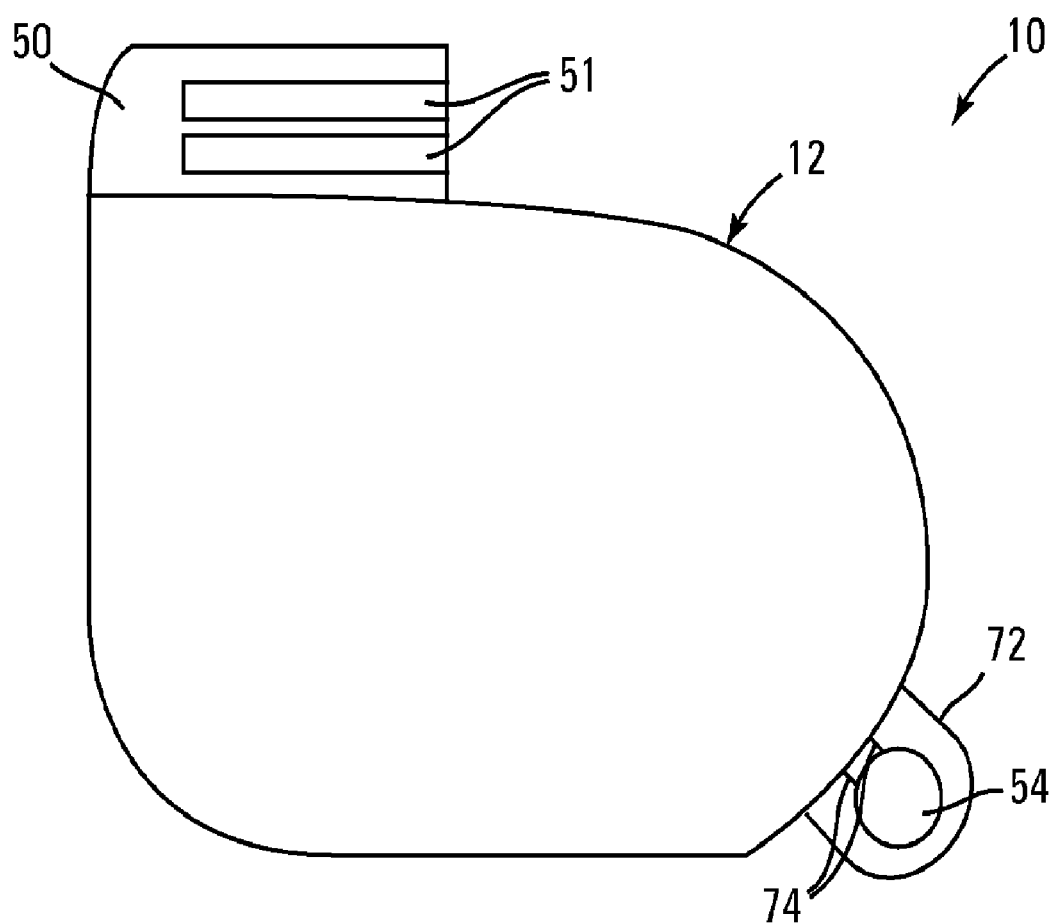
FIG. 7 shows a front view of yet another embodiment of an implantable medical device according to the present invention.

FIG. 7 depicts a front view of yet another embodiment of the implantable medical device 10. In this embodiment, the acoustic transducer 54 is located in a tab 72, which is attached to the housing 48 and is connected to the control circuitry via feedthroughs 74. The tab 72 may comprise the same material as is used in the header 50. In one embodiment, the tab 72 comprises Tecothane. Alternatively, the tab 72 can comprise any biocompatible material, such as titanium, and can be welded or otherwise attached to the housing 48. The tab 72 could include a plurality of acoustic transducers 54. The IMD 10 could include a plurality of tabs 72. Acoustic transducers 54 could be located in the header 50, in the tab or tabs 72, or both in the header 50 and tab or tabs 72. The acoustic transducers 54 can include any combination of PZT, PVDF, cMUT, or any other transducers as known in the art.

Figure 8:
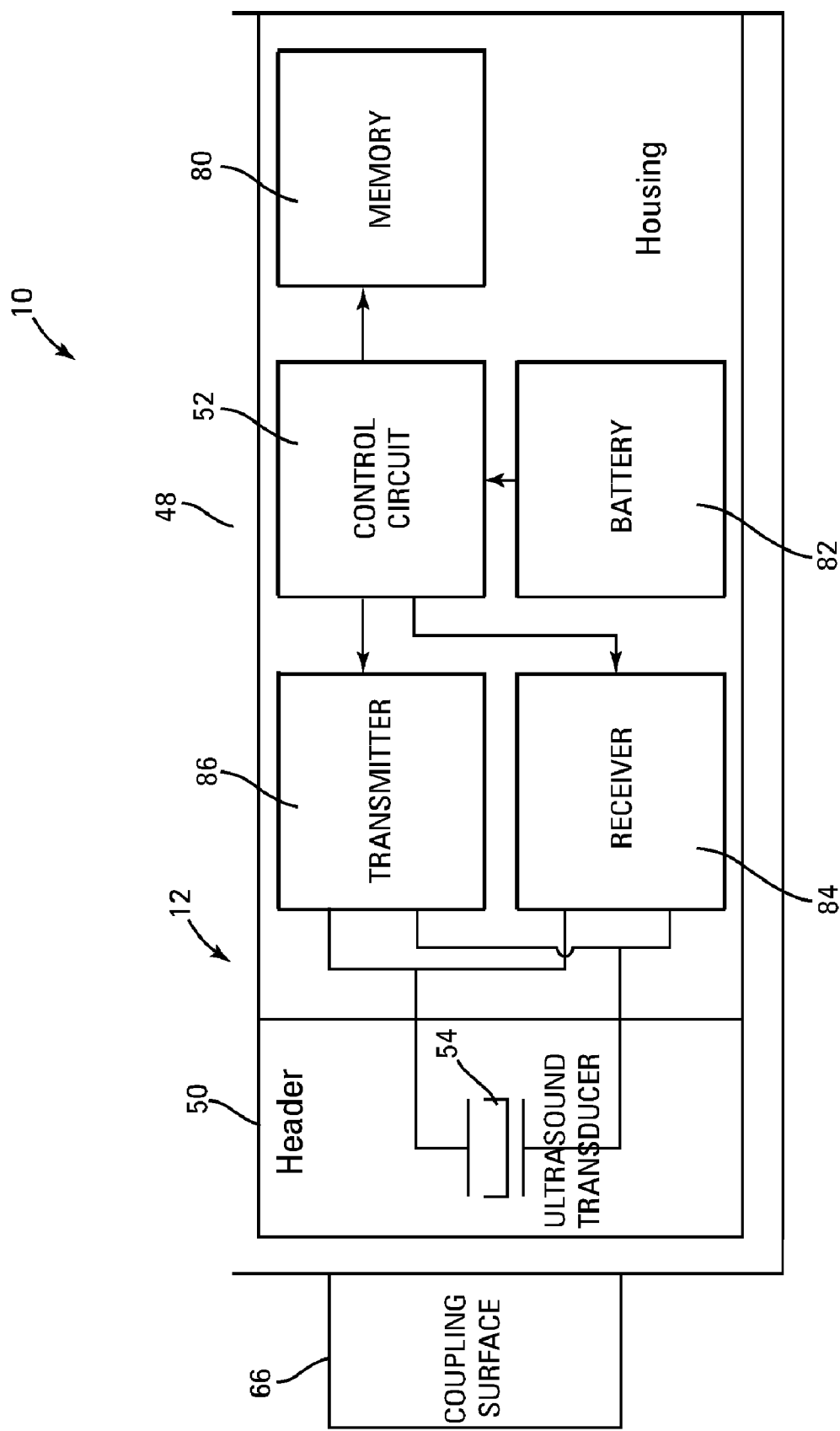
FIG. 8 depicts a block diagram of an implantable medical device according to the present invention.

FIG. 8 is a schematic of the implantable medical device 10. As described, the pulse generator 12 includes a housing 48 and a header 50. The housing 48 includes control circuitry 52, a memory 80, a battery 82, a receiver 84, and a transmitter 86. The acoustic transducer 54 is located in the header 50 and is electrically connected to the transmitter 86 and the receiver 84. The transmitter 86, receiver 84, and memory 80 are connected to the control circuitry 52. The control circuitry 52 is powered by the battery 82.

Figure 9:
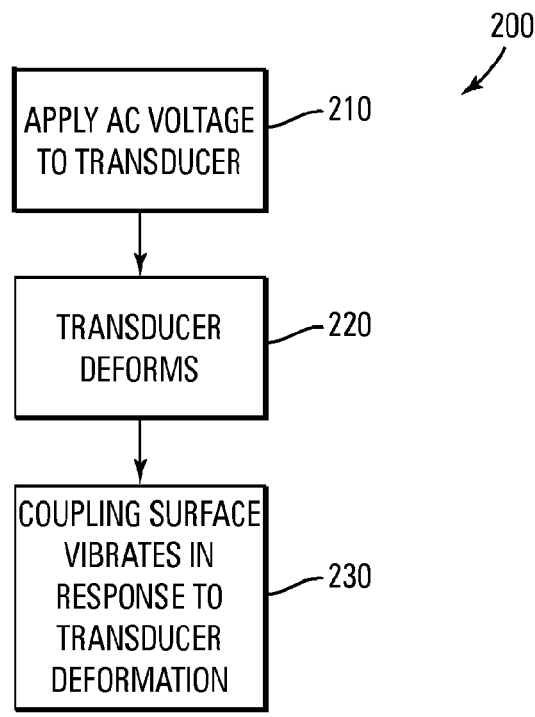
FIG. 9 is a flowchart depicting an exemplary method of using the implantable medical device of FIG. 2 to transmit acoustic signals.

FIG. 9 is a flowchart depicting an exemplary method 200 of using the implantable medical device 10 of FIG. 1 to transmit acoustic signals. The control circuitry 52 instructs the transmitter 86 to apply an AC voltage at the communication frequency to the acoustic transducer 54 (block 210). This voltage results in the periodic deformation of the acoustic transducer 54 (block 220) at the communication frequency. This periodic deformation results in vibration of the coupling surface 66 at the communication frequency, causing acoustic signals to travel through the tissue at the communication frequency (block 230). In one embodiment, the acoustic transducer 54 comprises a PVDF material 64 and the coupling surface 66 comprises a diaphragm that propagates the acoustic waves from the PVDF material 64 to the external tissue. In another embodiment, the acoustic transducer 54 comprises a PZT material 58 and the coupling surface 66 comprises a resonant surface that resonates at the communication frequency.

Figure 10:
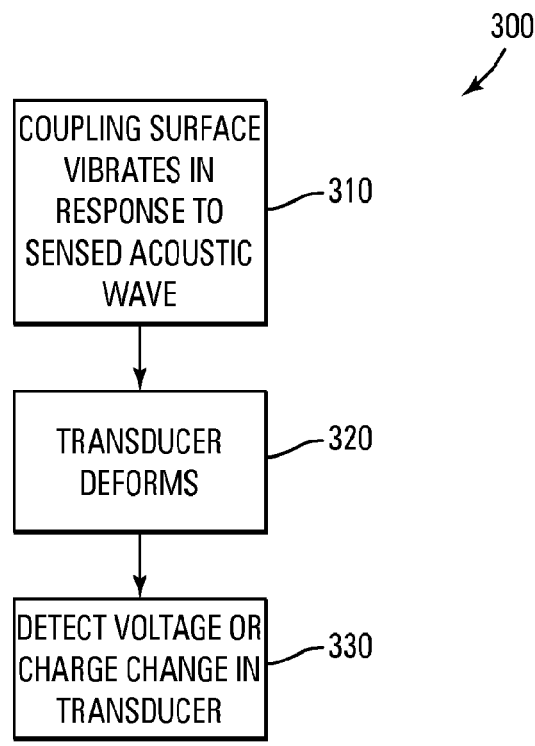
FIG. 10 is a flowchart depicting an exemplary method of using the implantable medical device of FIG. 2 to receive acoustic signals.

FIG. 10 is a flowchart depicting an exemplary method 300 of using the implantable medical device of FIG. 1 to receive ultrasonic signals. The impingement of acoustic signals on the coupling surface 66 causes it to vibrate at the communication frequency (block 310). In one embodiment, the acoustic transducer 54 comprises a PVDF material 64 and the coupling surface 66 comprises a diaphragm that propagates the acoustic waves from the external tissue to the PVDF material 64. In another embodiment, the acoustic transducer 54 comprises a PZT material 58 and the coupling surface 66 comprises a resonant surface that resonates at the communication frequency. The vibration of the coupling surface 66 results in periodic deformation of the acoustic transducer 54 (block 320). This periodic deformation causes a voltage or current change in the acoustic transducer 54 at the communication frequency, which is detected by the receiver 84 and processed by the control circuitry 52 (block 330). In the manner shown in FIGS. 9 and 10, the acoustic transducer 54 can be used to transmit signals from an implantable medical device 10 to a remote sensor 46 and receive signals from a remote sensor 46.

The invention has been described with respect to implantable medical devices such as pacemakers and defibrillators, but could be adapted for use in any other implantable medical device, such as an insulin pump, neurostimulator, drug delivery system, pain management system, heart or lung sound sensor, or any other implantable medical device. The remote device 46 can comprise any type of chronically implanted device or remote sensor adapted to deliver therapy or monitor biological functions, such as pressure sensor, glucose level monitor, a pulmonary sound sensor, volume sensor, satellite pacing device, or any other remote sensing or therapy-delivering device, and can be located anywhere in the body adapted for sensing a desired biological parameter or delivering therapy. A plurality of remote devices 46 could be implanted throughout the body and in wireless communication with each other and with an IMD 10.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device for implantation into body tissue comprising:
    a housing and a header coupled to the housing;
    a cavity located in the header;
    a casing disposed within the cavity, the casing having a wall defining a coupling surface;
    an ultrasonic transducer disposed inside the casing, the transducer adapted to transmit acoustic waves at a communication frequency; and
    control circuitry disposed in the housing, the control circuitry adapted to communicate with a remote device by driving the transducer at the communication frequency and processing electrical signals received from the transducer;

wherein the coupling surface is configured to be interposed between the ultrasonic transducer and the body tissue, the coupling surface having a resonance frequency greater than about 20 kHz and the coupling surface configured to be acoustically coupled with the body tissue.

2. The implantable medical device of claim 1 wherein the ultrasonic transducer comprises a polyvinylidine diflouride (PVDF) material.

3. The implantable medical device of claim 2 wherein the ultrasonic transducer further comprises a substrate located adjacent to a back wall of the casing, the substrate includes an aperture, and the PVDF material is disposed over the aperture.

4. The implantable medical device of claim 1 wherein the ultrasonic transducer comprises a lead zirconate titanate (PZT) material and the coupling surface comprises a surface that resonates at the communication frequency.

5. The implantable medical device of claim 4 wherein the PZT material is coupled to the coupling surface.

6. The implantable medical device of claim 1 wherein a plurality of cavities are located in the header, each cavity having a casing disposed therein and each casing having an ultrasonic transducer disposed therein, each casing having a coupling surface that is interposed between each ultrasonic transducer and the body tissue and is acoustically coupled with the body tissue.

7. The implantable medical device of claim 6 wherein the header includes a plurality of surfaces, and at least two of the surfaces include a cavity.

8. The implantable medical device of claim 1 wherein the approximate shape of the ultrasonic transducer is circular.

9. The implantable medical device of claim 1 wherein the communication frequency is approximately 40 kiloHertz.

10. The implantable medical device of claim 1 wherein the ultrasonic transducer is adapted to receive acoustic waves at the communication frequency.

11. The implantable medical device of claim 1 wherein the implantable medical device includes a pulse generator.

12. The implantable medical device of claim 1 wherein the transducer is disposed within the casing such that a space is maintained between the transducer and an inner surface of the casing, the space being filled with a medium having an impedance that generally matches the impedance of the human body.

13. The implantable medical device of claim 1 wherein the transducer is disposed within the casing on the coupling surface.

14. An implantable medical device for implantation into body tissue comprising:

a housing and a header coupled to the housing;

a cavity located in the header;

a casing disposed within the cavity, the casing having a surface defining a coupling surface;

a means for communicating ultrasonic signals, the means for communicating located in the casing; and control circuitry disposed in the housing, the control circuitry adapted to communicate with a remote device by driving the means for communication at the communication frequency and processing electrical signals received from the means for communication;

wherein the coupling surface is configured to be interposed between the means for communicating ultrasonic signals and the body tissue, the coupling surface a resonance frequency greater than about 20 kHz and the coupling surface is configured to be acoustically coupled with the body tissue.

15. The implantable medical device of claim 14 wherein the means for communicating an ultrasonic signal comprises a piezoelectric transducer.

16. The implantable medical device of claim 14 wherein the means for communicating an ultrasonic signal comprises a cMUT transducer.

17. The implantable medical device of claim 14 wherein the means for communicating an ultrasonic signal comprises a plurality of cavities located in the header, each cavity having a casing disposed therein and each casing having an ultrasonic transducer disposed therein, each casing having a coupling surface that is interposed between each ultrasonic transducer and the body tissue and is acoustically coupled with the body tissue.

18. The implantable medical device of claim 14 wherein the means for communicating is located within the casing such that a space is maintained between the means for communicating and the inner surface of the casing, the space being filled with a medium having an impedance that generally matches the impedance of the human body.

19. The implantable medical device of claim 14, wherein the transducer is located within the casing on the coupling surface.

* * * * *